United States Patent
Modarresi et al.

(10) Patent No.: US 9,988,330 B2
(45) Date of Patent: Jun. 5, 2018

(54) PROCESS AND APPARATUS FOR THE PRODUCTION OF HIGHER ALCOHOLS

(71) Applicant: Haldor Topsøe A/S, Kgs. Lyngby (DK)

(72) Inventors: Hassan Modarresi, Lyngby (DK); Christian Wix, Nærum (DK)

(73) Assignee: Haldor Topsoe A/S, Lyngby (DK)

( * ) Notice: Subject to any disclaimer, the term of this patent is extended or adjusted under 35 U.S.C. 154(b) by 307 days.

(21) Appl. No.: 14/651,083

(22) PCT Filed: Dec. 18, 2013

(86) PCT No.: PCT/EP2013/077060
§ 371 (c)(1),
(2) Date: Jun. 10, 2015

(87) PCT Pub. No.: WO2014/095978
PCT Pub. Date: Jun. 26, 2014

(65) Prior Publication Data
US 2015/0315109 A1  Nov. 5, 2015

(30) Foreign Application Priority Data
Dec. 20, 2012 (DK) .................................. 2012 00812

(51) Int. Cl.
*C07C 29/152* (2006.01)
*C07C 29/32* (2006.01)

(52) U.S. Cl.
CPC ............. *C07C 29/152* (2013.01); *C07C 29/32* (2013.01)

(58) Field of Classification Search
CPC .............................. C07C 29/152; C07C 29/32
See application file for complete search history.

(56) References Cited

U.S. PATENT DOCUMENTS

| | | | |
|---|---|---|---|
| 5,635,145 A * | 6/1997 | Den Hartog | B01J 8/0492 261/97 |
| 2009/0018371 A1 * | 1/2009 | Klepper | C07C 29/1518 568/902.2 |
| 2009/0048354 A1 | 2/2009 | Reddy et al. | |
| 2009/0069452 A1 | 3/2009 | Robota | |
| 2010/0069515 A1 | 3/2010 | Tirtowidjojo et al. | |
| 2010/0160694 A1 * | 6/2010 | Fitzpatrick | C07C 29/1516 568/913 |
| 2011/0065966 A1 | 3/2011 | Mueller et al. | |

FOREIGN PATENT DOCUMENTS

| | | |
|---|---|---|
| CN | 101218198 A | 7/2008 |
| CN | 101730674 A | 6/2010 |
| WO | WO 2007/003909 A1 | 1/2007 |
| WO | WO 2012/003901 A1 | 1/2012 |
| WO | WO2012003901 * | 1/2012 |
| WO | WO 2012/062338 A1 | 5/2012 |

* cited by examiner

*Primary Examiner* — Pancham Bakshi
*Assistant Examiner* — Mark R Luderer
(74) *Attorney, Agent, or Firm* — Blank Rome LLP

(57) ABSTRACT

In a process for the production of higher alcohols, i.e. $C_{4+}$ alcohols, from syngas, the syngas is first reacted in a heterogeneous alcohol pre-converter (A) using an alcohol synthesis catalyst, whereby methanol as the main product in a concentration corresponding to or close to the equilibrium concentration is produced. Then the effluent from the pre-converter is mixed with unconverted wet recycle gas and reacted in a heterogeneous reactor for higher alcohols synthesis (B) containing a higher alcohols synthesis catalyst, and finally the effluent from the reactor for higher alcohols synthesis is separated into (i) unconverted syngas, which is recycled to the higher alcohols synthesis reactor, (ii) methanol and light alcohols, which are recycled to the higher alcohols synthesis reactor, and (iii) the final product consisting of higher alcohols.

12 Claims, 3 Drawing Sheets

PROCESS AND APPARATUS FOR THE PRODUCTION OF HIGHER ALCOHOLS

The present invention relates to a process for the production of higher alcohols. More specifically, the invention concerns the catalytic production of higher alcohols from a gas mixture of hydrogen and carbon monoxide, commonly known as synthesis gas or syngas. Further the invention relates to process layouts for an apparatus for carrying out the process.

Because higher alcohols can be used either directly as substitutes for hydrocarbon fuels or indirectly as additives to hydrocarbon fuels, they are desirable compounds for the fuel market in the future. Fuel mixtures containing higher alcohols are especially preferred due to their increased water tolerance and their improved heating value. Furthermore, higher alcohols are valuable stand-alone chemicals with a variation of applications, and therefore selective synthesis processes for higher alcohols are very desirable.

The production of higher alcohols, i.e. $C_{4+}$ alcohols, according to the present invention proceeds from syngas via methanol using a heterogeneous catalyst developed for the synthesis of such alcohols. The reactions involved are exothermic, and it is therefore important to remove the heat of said reactions from the reactor in order to avoid any temperature rise in the catalytic bed above a certain critical value and consequently to prevent a fast sintering and deactivation of the catalyst. This gives the reactor for the higher alcohols synthesis a rather narrow operating temperature window.

Based on experience from methanol production processes it could be a good option to choose a boiling water reactor (BWR) as synthesis reactor. There are, however, some practical difficulties in employing this kind of reactor. First of all, the operating temperature is considerably higher than in a methanol reactor, which means a much higher pressure in the shell side of the reactor, i.e. the boiling water side. The steam pressure will also be considerably higher than in the methanol BWR case. The result would be a reactor with thicker shell and thus a more expensive reactor.

Another difficulty is that the degree of conversion in the higher alcohols synthesis in a BWR is low, and therefore the recycle flow of unreacted gas is 5-10 times larger than in a methanol plant. This means that a BWR reactor for higher alcohols production needs to be much bigger.

Various processes for the production of alcohols from syngas are described in the prior art. Thus, US 2009/0048354 describes a process for the conversion of syngas to oxygenates containing $C_{2+}$ alcohols in the presence of a particulate catalyst. The process is performed in a methanol synthesis reactor and a higher alcohols synthesis reactor arranged in parallel.

Figure 3:
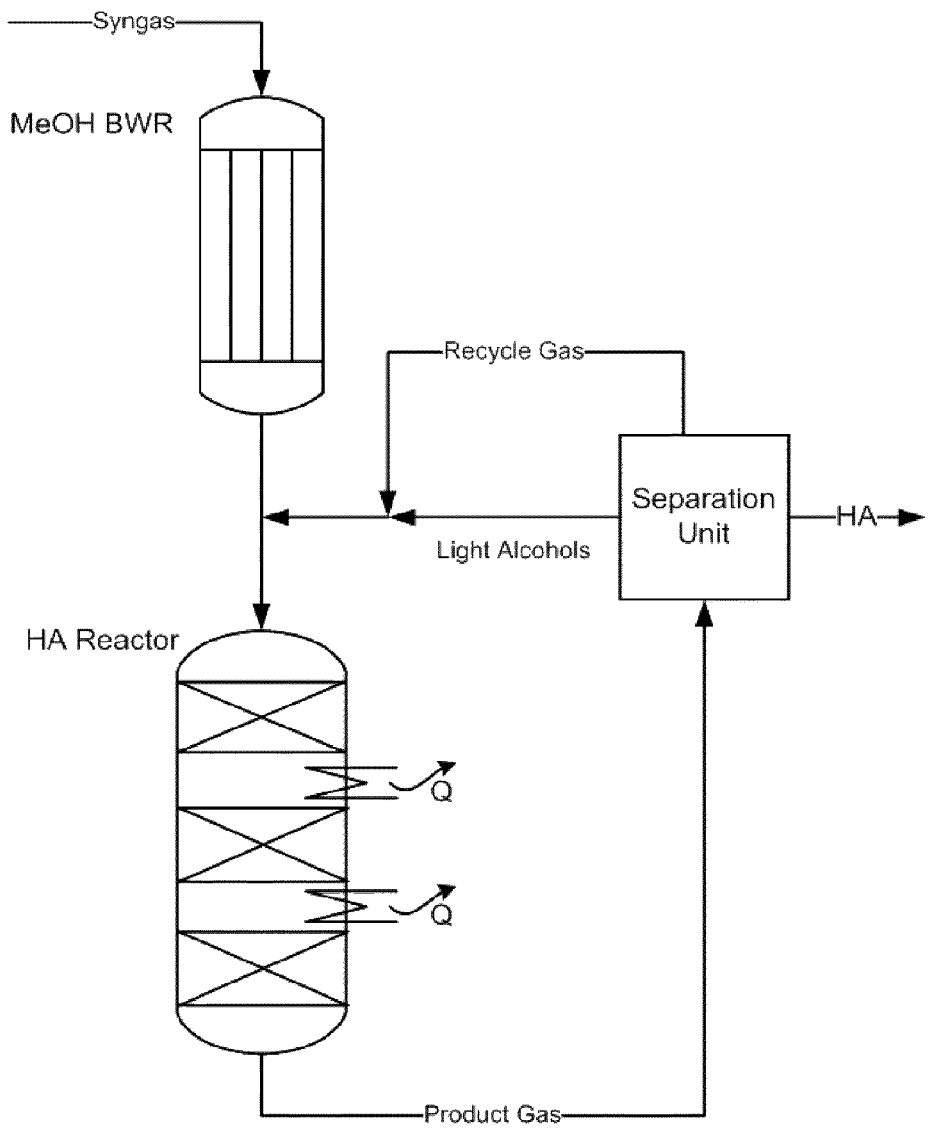

US 2009/0069452 discloses methods and process layouts for producing ethanol and/or other higher alcohols from syngas. FIG. 3 of said document specifically shows a process layout where methanol is injected into the reactor for higher alcohols synthesis, however without explaining how and why this is done.

In US 2010/0069515 a mixed alcohol synthesis with enhanced carbon value use is described. Specifically said document discloses a process layout where light alcohols are recycled to the reactor for higher alcohols synthesis, however without including a pre-converter in the process layout.

These three prior art documents all disclose the use of two reaction zones or even two separate reactors in either series or parallel connection, one of which is used for methanol synthesis while the other is used for higher alcohols synthesis. Furthermore, a part of the methanol or the light alcohols is being recycled to the reactor for higher alcohols synthesis according to these documents.

Further, WO 2007/003909 describes a process for producing higher alcohols from syngas, which is led to a methanol reactor. The methanol produced is led to a homologation reactor for producing higher alcohols, and unconverted syngas from the homologation reactor is recycled to be mixed with the methanol stream. The effluent from the homologation reactor is separated into unconverted syngas, methanol, which is recycled to the homologation reactor, and a product stream comprising higher alcohols (ethanol and propanol). This process, however, is quite complicated, comprising at least eight steps.

US 2009/0018371 describes another process for producing higher alcohols from syngas, where syngas is passed through a first reaction zone in a reactor for converting syngas to methanol. The effluent is led to a second reaction zone in another reactor for converting syngas and methanol to higher alcohols. Unconverted syngas is recycled to the second reactor together with methanol from the product stream. The product stream from the second reactor is separated into different fractions, e.g. methanol, ethanol, higher alcohols, water and unreacted syngas. The separated methanol fraction from the product stream is recycled to the second reactor as mentioned.

In both WO 2007/003909 and US 2009/0018371 the purpose of the methanol pre-converter is to produce methanol first and then use it in the second reactor to produce higher alcohols, whereas in the present invention the sole purpose of the methanol pre-converter is to remove the methanol synthesis heat which would otherwise occur in the higher alcohols reactor and make the higher alcohols synthesis difficult because of the problem with removal of heat from the reactor. Therefore, the condition of the methanol pre-converter has to be set in such a way that the inlet feed to the higher alcohols reactor after being mixed with recycle gas and other possible alcohols is equal to or at least close to the equilibrium composition of methanol in the higher alcohols inlet condition. This limits the heat release from the higher alcohols reactor to an insignificant heat release from the higher alcohols synthesis with low conversion.

Finally, US 2011/0065966 describes a process for producing methanol from syngas containing hydrogen and carbon oxides, where the syngas is passed through a first, preferably water-cooled reactor, in which a part of the carbon oxides is converted catalytically to methanol. The obtained mixture containing syngas and methanol vapour is supplied to a second, preferably gas-cooled reactor, in which a further part of the carbon oxides is converted to methanol. Subsequently, methanol is separated from the syngas, and the syngas is recycled to the first reactor. To achieve a maximum methanol yield, even with an aged catalyst, a partial stream of the syngas is guided past the first reactor and introduced directly into the second reactor. The purpose is to produce methanol in two steps, first in a boiling water reactor at a high temperature with strong syngas (high $CO/H_2$ concentration) where the heat can be effectively removed from the reactor, and then in a gas-cooled reactor at a lower temperature with weak syngas, where the reaction heat release is not severe. The purpose of the second gas-cooled methanol reactor is to have a high syngas-to-methanol conversion by continuing methanol synthesis at a lower temperature with a more active catalyst. In a higher alcohols reactor, equilibrium reactions are not the main reactions; therefore, the purpose and scope of the process design are completely different.

It has now surprisingly been found that a gas mixture of hydrogen and carbon monoxide, i.e. syngas, can be converted very efficiently to higher alcohols, i.e. $C_{4+}$ alcohols, by a process wherein a) the syngas is preferably reacted in a heterogeneous alcohol pre-converter, whereby mainly methanol in a concentration corresponding to or close to the equilibrium concentration is produced, b) the effluent from the pre-converter, or the syngas if the pre-converting step (a) is omitted, is mixed with unconverted recycle syngas and reacted in a heterogeneous reactor for higher alcohols synthesis using a higher alcohols synthesis catalyst, and c) the effluent from the reactor for higher alcohols synthesis is separated into (i) unconverted syngas, which is recycled to the higher alcohols synthesis reactor, (ii) methanol and light alcohols ($C_{2/3}$ alcohols), which are recycled to the higher alcohols ($C_{4+}$ alcohols) synthesis reactor, and (iii) the final product consisting of higher alcohols.

The unconverted syngas (i.e. recycle gas) is depleted from carbon dioxide and saturated with light alcohols before it is sent to the higher alcohols synthesis reactor.

It is noted that in the process outlined above, step (a) concerning the methanol pre-converter reactor, may be omitted from the process.

One important point about the higher alcohols reactor, which should be noted, is that the conversion in this reactor is not high. Therefore a big volume of catalyst is required. The use of a methanol pre-converter as in the present invention eliminates the need to use an expensive boiling water reactor for the higher alcohols synthesis.

Another differentiating aspect between the prior art and the present invention is the way recycle gas is used in the process. It appears from the prior art that recycle gas is fed also to the methanol pre-converter, whereas in the present invention there is no need for this, since the process in fact does not need methanol synthesis prior to the higher alcohols reactor from a reaction point of view, i.e. for higher alcohols production. The methanol pre-converter addresses one of the practical challenges of higher alcohols reactors, which is the low degree of syngas-to-higher alcohols conversion requiring a big reactor volume.

Still another differentiating aspect between the prior art and the present invention is that the separating section of the process of the present invention removes part of or even all of the carbon dioxide content from the recycle gas. This is important, because carbon dioxide is a higher alcohols reaction hindering agent.

Steam generated from the heat of reactions (from either methanol synthesis or higher alcohols synthesis or both) may be used to drive a compressor for unconverted recycled syngas.

Figure 1:
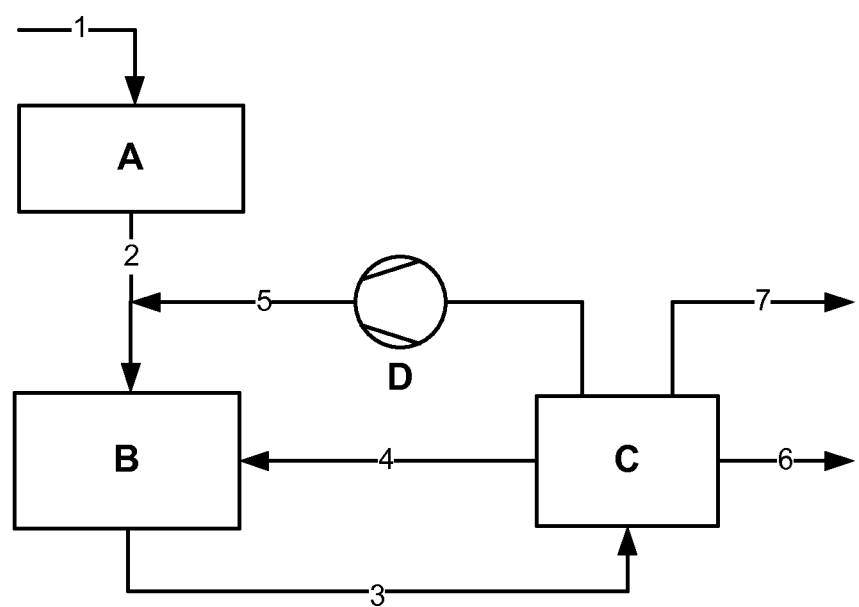

In the following, referring to FIG. 1, the process according to the invention is described in more detail. FIG. 1 shows a general form of the process layout.

In the process according to the invention, syngas (1) is optionally pre-converted to alcohols, mainly methanol, in the alcohol pre-converter (A). The effluent product (2) is further reacted along with wet recycle gas (5) and light alcohols (4) in the higher alcohols reactor (B) to produce higher as well as lighter alcohols as effluent (3). This gaseous effluent (3) is cooled down and condensed to a liquid product and a gas product. The gas product as unconverted recycle syngas is pressurised by means of the recycle compressor (D) and returned to the higher alcohols synthesis reactor (B) after having been depleted from carbon dioxide. The liquid product is fractionated into light and heavy alcohol products. The stream of light alcohols (4) is recycled to the reactor (B) and used partly in liquid form for cooling the reactants and for producing higher alcohols in gas form. The final product stream of heavy alcohols (6) is drawn from the separation unit (C). The stream (7) from the separation unit (C) consists of the purge materials.

Figure 2:
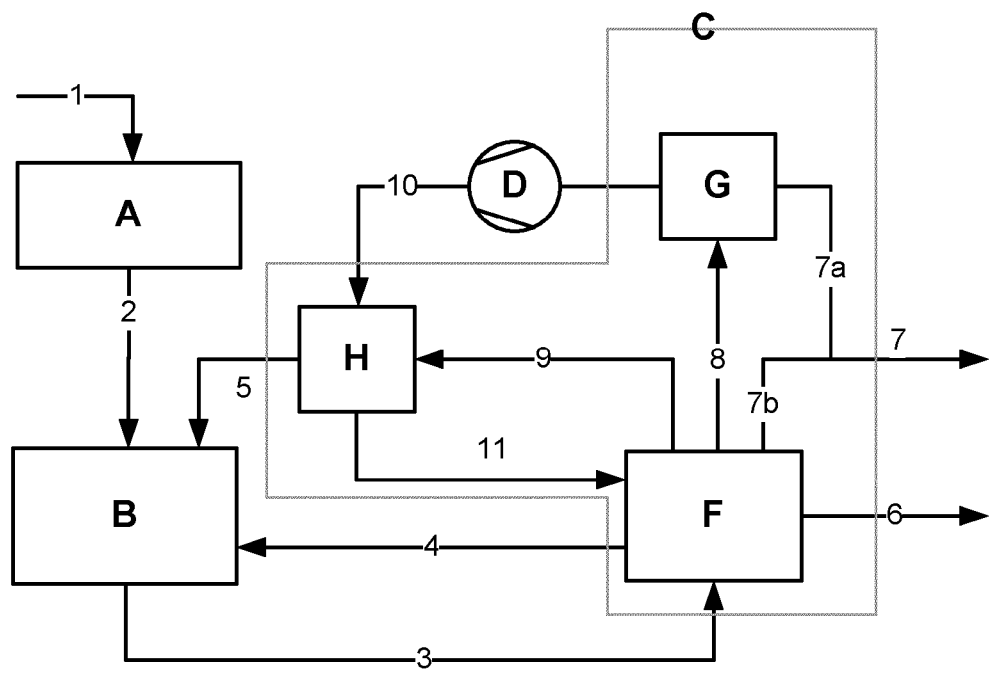

In FIG. 2, the separation unit (C) is shown in detail as three units, more specifically the gas/liquid separator and distillation unit (F), the carbon dioxide removal unit (G) and the saturator unit (H).

The unconverted gaseous reactants from the reactor (B) are separated in the unit (F) as stream (8) and sent to the carbon dioxide separation unit (G). The carbon dioxide is either partially or completely removed and purged through the line (7a). The treated gas is compressed in the compressor (D) and sent through the line (10) to the separator (H). Dry treated and pressurized gas is contacted with alcohol mixtures (mainly light alcohols) in the saturator (H). The result is a wet recycle gas saturated with light alcohols (5), which is fed to the higher alcohols reactor (B) and a concentrated mixture of higher alcohols (11), which is fed to the distillation unit (F) for further separation and purification.

It is thus seen that the unreacted gas is recycled to the second reactor, i.e. the higher alcohols reactor (B), in the process layout. None of the prior art citations show this detail.

The distillation unit (F) also provides a stream of light alcohols (4) for cooling the higher alcohols reactor (B). The final product from this unit is collected through the line (6), while by-products and off-gases are sent out via the stream (7b).

All methanol as well as light alcohols are recycled to the higher alcohols synthesis reactor. This is because methanol and light alcohols are not products from the process of the invention, but rather intermediates. In the prior art citations both methanol and light alcohols are products.

Regarding the reactors, the process according to the invention allows for reactor types for both methanol synthesis and higher alcohols synthesis. None of the prior art citations give any details in this respect.

The higher alcohols synthesis reactor is preferably either a single or a multi-bed/multi-stage adiabatic reactor with inter-bed/inter-stage cooling. Said inter-bed/inter-stage cooling can be achieved by injection of a recycled light alcohol solution, preferably a methanol-rich solution, or a cold unconverted syngas. It can also be achieved through indirect cooling, such as steam generation.

The higher alcohols synthesis reactor is preferably either a gas/liquid cooled reactor or a boiling water reactor (BWR). If it is a gas-cooled higher alcohols synthesis reactor, then it can be cooled by cold unconverted recycle gas.

Regarding the heterogeneous methanol pre-converter, this can either be an adiabatic reactor or any isothermal or semi-isothermal reactor, such as a boiling water reactor, a gas-cooled reactor or the like.

Some reactor details are shown in FIG. 3. The embodiment shown in FIG. 3 is merely an example of how the layout for the process according to the present invention can be envisaged. The layout is not limited to the embodiment shown in FIG. 3 in any way.

A methanol pre-converter reactor followed by a multi-bed higher alcohols (HA) reactor with inter-bed cooling for HA production is shown in FIG. 3. The pre-converter reactor is a boiling water reactor (BWA). The HA reactor is a multi-bed quench reactor (MQR). Intermediate cooling can be done either indirectly or directly. In the indirect cooling system, the exit gas from one bed is cooled either internally or externally with a cooling medium. In the indirect cooling system, either cold recycle gas or a liquid mixture of light alcohols is injected between the beds.

The invention is explained further by the following example, to which the invention is not limited in any way.

EXAMPLE

According to the process block diagram shown in FIG. 1, syngas (1) is introduced in the boiling water reactor (A) for methanol synthesis, which reactor operates at a space time velocity of 2.1 kg methanol/kg catalyst/h, a temperature of 250° C. and a pressure of 91.5 barg. The effluent from this reactor is mixed with unconverted recycle syngas (5) and fed to the higher alcohols (HA) reactor (B), which is a 4-bed adiabatic reactor with a total catalyst volume of 19.4 m³. The reactor operates at an average temperature of 300° C. and a pressure of 90 barg. The recycled light alcohols solution is injected between the beds to cool down the reactants. The product effluent gas from the HA reactor (3) is cooled down and then condensed to a liquid product and a gas product.

The gas product as unconverted recycle syngas is pressurized by means of the recycle compressor (D) and returned to the HA synthesis reactor after having been depleted from carbon dioxide. The liquid product is fractionated into two products consisting of light alcohols and heavy alcohols. The stream (4) of light alcohols is recycled to the reactor and used, partly in liquid form, for cooling the reactants and for producing higher alcohols in gas form. The final product (6) consisting of heavy alcohols is drawn from the separation unit (C). The stream (7) contains the purge materials, both liquid and gaseous materials.

The following table 1 lists the flow and the composition of the individual streams. In this process the stream of higher alcohols (HA) refers to isobutanol and alcohols higher than isobutanol, while the stream of light alcohols (LA) refers to alcohols between methanol and isobutanol, i.e. mainly ethanol, 1-propanol and 2-propanol.

TABLE 1

| | Stream | | | | | |
|---|---|---|---|---|---|---|
| | 1 | 2 | 3 | 4 | 5 | 6 |
| Flow (kg/h) | 5213 | 5213 | 47603 | 17186 | 25204 | 1323 |
| | weight % | | | | | |
| CO | 86.8 | 69.4 | 40.3 | 0.0 | 71.7 | 0.0 |
| $CO_2$ | 6.1 | 8.6 | 6.9 | 0.0 | 2.3 | 0.0 |
| $H_2$ | 4.1 | 2.0 | 1.8 | 0.0 | 2.3 | 0.0 |
| methanol | 0.0 | 14.3 | 9.6 | 27.1 | 0.0 | 0.0 |
| LA | 0.0 | 2.1 | 11.0 | 31.4 | 0.0 | 0.0 |
| HA | 0.0 | 0.4 | 17.3 | 40.5 | 0.0 | 99.9 |
| inert/by-product | 3.0 | 3.2 | 13.1 | 1.0 | 22.8 | 0.1 |

The invention claimed is:

1. A process for the production of higher alcohols from a gas mixture of hydrogen and carbon monoxide, so-called syngas, comprising:
   a) reacting syngas in a heterogeneous alcohol pre-converter containing a methanol synthesis catalyst and producing an effluent comprising methanol in a concentration corresponding to or about the equilibrium concentration at a given temperature and concentration, and removing heat of the methanol synthesis reaction,
   b) mixing the effluent from the pre-converter reactor with unconverted recycle syngas to form a mixture and reacting the mixture in a heterogeneous higher alcohols synthesis reactor in the presence of a higher alcohols synthesis catalyst, to form a product gas containing carbon dioxide, and
   c) feeding the product gas to a separation unit and separating the product stream into recycle streams of (i) unconverted syngas, which is recycled to the higher alcohols synthesis reactor and (ii) methanol and light alcohols, which are recycled to the higher alcohols synthesis reactor, and into a final product stream consisting of higher alcohols, wherein the separation unit removes carbon dioxide from the recycle streams.

2. The process according to claim 1, wherein the alcohol pre-converter is either a gas-liquid cooled reactor or a boiling water reactor (BWR).

3. The process according to claim 1, wherein the higher alcohols synthesis reactor is a single bed adiabatic reactor, a single stage adiabatic reactor, a multi-bed adiabatic reactor with inter-bed cooling, or a multi-stage adiabatic reactor with inter-stage cooling.

4. The process according to claim 1, wherein the recycle syngas is a wet recycle gas saturated with methanol and light alcohols.

5. The process according to claim 3, wherein the higher alcohols synthesis reactor includes multiple beds or multiple stages, and cooling is achieved by either injection of a recycled light alcohol solution, or an unconverted syngas.

6. The process according to claim 5, wherein the reactor is cooled by unconverted recycle gas.

7. The process according to claim 1, wherein the heterogeneous alcohol pre-converter is either an adiabatic reactor, an isothermal reactor, or a semi-isothermal reactor.

8. The process according to claim 1, wherein the condition of the methanol pre-converter is set in such a way that the inlet feed to the higher alcohols synthesis reactor, after being mixed with recycle gas and other alcohols, is equal to or at least about the equilibrium composition of methanol at the inlet to the higher alcohols synthesis reactor.

9. The process according to claim 1, wherein steam is generated from the removal of the heat of the reaction and is used to drive a compressor for unconverted recycled syngas.

10. An apparatus for carrying out the method according to claim 1, said apparatus comprising a pre-converter for pre-converting syngas to alcohols, a higher alcohols reactor for further reaction of the effluent with wet recycle gas and light alcohols and a separation unit to separate unconverted reactants in the effluent into recycle gas streams, purge streams and a product stream, the apparatus further comprising a compressor in fluid communication with the separation unit which comprises: a gas/liquid separator, a distillation unit, a carbon dioxide removal unit, and a saturator unit, where pressurize recycle syngas is contacted pressurized gas is contacted with recycle alcohol mixtures.

11. The apparatus according to claim 10, wherein the pre-converter is a boiling water reactor and the higher alcohols reactor is a multi-bed quench reactor.

12. The process according to claim 3, wherein the higher alcohols synthesis reactor includes multiple beds and multiple stages, and cooling is achieved by indirect cooling.

* * * * *